United States Patent [19]
Nanba et al.

[11] Patent Number: 5,854,404
[45] Date of Patent: Dec. 29, 1998

[54] ANTITUMOR SUBSTANCE EXTRACTED FROM GRIFOLA

[75] Inventors: Hiroaki Nanba; Keiko Kubo, both of Hyogo, Japan

[73] Assignee: Yukiguni Maitake Co., Ltd., Niigata, Japan

[21] Appl. No.: 812,795

[22] Filed: Mar. 6, 1997

[30] Foreign Application Priority Data

Mar. 8, 1996 [JP] Japan ................................. 8-051880

[51] Int. Cl.$^6$ ................................................ C07K 1/00
[52] U.S. Cl. ........................... 532/424; 514/12; 530/300; 530/350; 530/412; 530/418
[58] Field of Search ............................. 514/12; 530/412, 530/414, 418, 424, 300, 350

[56] References Cited

PUBLICATIONS

Nanba et al Chem Pharm Bull. vol. 35 (3) 1162–1168, 1987.

*Primary Examiner*—Sheela Huff
*Assistant Examiner*—Julie E. Reeves
*Attorney, Agent, or Firm*—Davidson, Davidson & Kappel, LLC

[57] ABSTRACT

An antitumor substance having high immunopotentiating activity, extracted and fractionated from mycelia or fruit bodies of Grifola with water can be obtained by adding alcohol to its extract at a final concentration of 20 to 60%, preferably at a final concentration of 20 to 50% by volume (low-concentration addition) to remove floating or adhering matter from it.

17 Claims, No Drawings

ANTITUMOR SUBSTANCE EXTRACTED FROM GRIFOLA

FIELD OF THE INVENTION

The present invention relates to an antitumor substance having high immunopotentiating activity, which was extracted and fractionated from mycelia or fruit bodies of a "Maitake" mushroom (Grifola).

BACKGROUND OF THE INVENTION

Polysaccharides consisting of β-1,6-linked glucose main chain with β-1,3-linked glucose branches or consisting of β-1,3-linked glucose main chain with β-1,6-linked glucose branches extracted from mycelia or fruit bodies of Grifola, is known to have anticancer activity (see Japanese Patent LOP Publication No. 210901/1984).

A process for producing an anticancer substance, which comprises a combination of the steps of extracting Grifola, *Grifola gigantea* (Tonbimai) or *Laetiporus sulphureus* (Masutake) with hot water, concentrating the extract under reduced pressure, precipitating the concentrate with an organic solvent, dialyzing the precipitates to remove low-molecular-weight substances, and extracting impurities with a lipophilic organic solvent to remove them from the Jialysate, is also known (see Japanese Patent Publication No. 16047/1968).

However, the prior processes described in Japanese Patent LOP Publication No. 210901/1984 and Japanese Patent Publication No. 16047/1968 are not necessarily appropriate for providing a larger amount of pharmaceutical preparations and health foods efficiently from limited resources because their purification steps are considerably complicated and the products contain substances inhibiting immunopotentiating activity.

SUMMARY OF THE INVENTION

Under these circumstances, the present inventors did extensive research on a method of extracting Grifola and on various extracts obtained in its process, and as a result, it was made possible to efficiently obtain an antitumor substance with superior immunopotentiating activity. The main feature is to enhance antitumor activity and an immunopotentiating activity by removing floating or adhering matter by adding alcohol at a final concentration of 20 to 60% by volume (low-concentration addition) to a water-soluble extract resulting from thermal extraction of mycelia or fruit bodies of Grifola with water.

That is, the present invention relates to a glucan/protein complex having immunopotentiating activity, which is prepared in the steps of:
(1) thermally extracting mycelia or fruit bodies of Grifola with water;
(2) adding alcohol to the resulting water-soluble extract at a final concentration of 20 to 60% by volume (low-concentration addition), allowing it to stand at a temperature of 1° to 25° C., and removing floating matter on the liquid or in the liquid or adhering matter to the vessel wall; and
(3) adding alcohol to the solution at a final concentration of 80 to 99% by volume (high-concentration addition), allowing it to stand at 1° to 25° C., and recovering the resulting precipitates, or after the step (2), concentrating the alcohol solution to form precipitates or concentrating it into dryness in a usual manner, as well as to an antitumor agent comprising the same as an active ingredient.

In the present invention, the "Maitake" mushroom (Grifola) may be *Grifola frondosa, Grifola albicans Imaz., Grifola umbellatus, Grifola gigantea* etc., and these can be used in fresh or dried form, if necessary cut into pieces, or in powder form.

The thermal extraction is carried out at 50° to 135° C. for 15 minutes to 3 hours. For rapid extraction, this treatment is carried out under pressure at 100° C. or more, for example, at 2 atmospheric pressure at about 120° C. in a pressure pot for 30 minutes to 1 hour or thereabout.

The water used is distilled water, purified water, ion-exchanged water, tap water etc. About 4 to 20 parts, preferably 4 to 10 parts by volume of water is used per part of dried Grifola by weight. If fresh Grifola is used, about 2 to 10 parts, preferably 2 to 5 parts by volume of water is used per part of Grifola by weight.

In the step (2), alcohol added to the extract can be methanol, ethanol etc. Alcohol is added to the extract at a final concentration of 20 to 60% by volume. Alcohol with a water content of 0 to 50% can be used. When left at a temperature of 1° to 25° C. for 1 to 20 hours after addition, there occurs floating matter on the liquid or in the liquid or adhering matter to the vessel wall and these are removed by filtration or with a pipette, net, etc.

Because removal of the floating and adhering matter brings about an enhancement in the antitumor activity and immunopotentiating activity of the extract, the step of removing said matter is extremely important. For this step, it is essential to add alcohol at a final concentration of 20 to 60% by volume, preferably at final concentration of 20 to 50%.

To the solution obtained in the step (2) is added alcohol at a final concentration of 80 to 99%, preferably at a final concentration of 80 to 90% by volume (high-concentration addition), and then it is allowed to sand at 1° to 25° C., preferably at 1° to 5° C. to precipitate the desired substance, or alternatively the solution obtained in the step (2) is concentrated under heating to form precipitates or concentrated into dryness under heating.

The properties of the resulting substance of the present invention are as follows:
Appearance: hygroscopic powder in shades of brown.
Solubility: dissolved in water, an alkaline solution and dimethyl sulfoxide.
Coloration reaction: positive in anthrone reaction and ninhydrin reaction.
Aqueous solution property: neutral to weakly acidic.
Molecular weight: distributed around 1,000,000.

Analysis of the substance obtained in the present invention indicated that its main components are glucan and protein. After purification by column chromatography, it was found that the major component of the antitumor substance having immunopotentiating activity obtained by the present invention is a glucan/protein complex where the glucan/protein ratio varies mainly in the range of 80:20 to 99:1 depending on the qualities of Grifola as the starting material, conditions for extraction and purification, etc.

EMBODIMENTS FOR CARRYING OUT THE INVENTION (1) Extraction Method 500 g of fruit bodies of dried *Grifola frondosa* were extracted with 5 L of distilled water at 120° C. for 60 minutes, and to 950 ml of the resulting soluble fraction was added ethanol at a final concentration of 45% by volume. When this solution was allowed to stand at 4° C. for 12 hours, viscous and dark brown matter was formed on the liquid, in the liquid or on the vessel wall. This substance was removed with a pipette. After addition of ethanol at a final concentration of at least 80% by volume, the solution was allowed to stand at a low temperature of 4° C. to give 3 g precipitates in shades of dark brown to black. The resulting substance was positive in both anthrone reaction and ninhydrin reaction. After purification by column chromatography, this substance was found to be glucan/protein complex where the glucan/protein ration was 96:4.

As a result of its examination by gel filtration chromatography on a TSK gel GMPW$_{XL}$ column, it was found that its molecular weight is distributed around 1,000,000. When its glucan moiety was hydrolyzed and examined qualitatively for neutral glucan by high performance liquid chromatography, only glucose was detected.

The examination of its protein moiety by an automatic amino acid analyzer (only tryptophan was examined by high performance liquid chromatography) indicated that the protein is composed of glutamic acid, aspartic acid, alanine, leucine, lysine, glycine, isoleucine, serine, valine, proline, threonine, arginine, phenylalanine, tyrosine, histidine, tryptophan, methionine, crystine etc.

(2) Antitumor Test

The substance obtained in (1) above (referred to hereinafter as "Substance A") and a dried substance obtained in the same manner as in (1) above except that the step of adding alcohol at low concentration (final concentration of 20 to 60% by volume) for removing floating matter on the liquid or in the liquid or adhering matter to the vessel wall was not carried out (referred to hereinafter as "Substance B") were dissolved respectively in physiological saline. Each solution was administered intraperitioneally into C3H mice with transplanted MM-46 carcinoma 10 times at a dosage of 0.1 mg/kg to examine its effect on tumor growth inhibition. The results are shown in Table 1.

TABLE 1

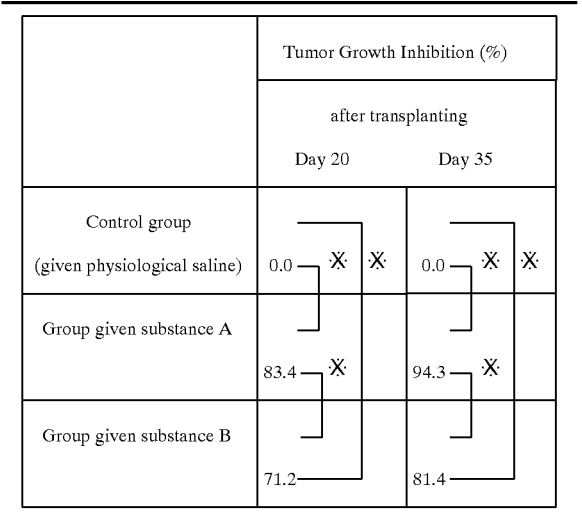

(15 mice per group, ※ t-test: there was a significant difference of 5% or less).

The tumor growth inhibition (%) was determined according to the following formula:

Tumor Growth Inhibition (%)=[1-(average tumor weight (g) in treatment group/average tumor weight (g) in control group)]×100 the group given Substance A indicated a significantly stronger inhibitory effect on tumor growth than that of the group given Substance B. Five days after each test substance was given, macrophages and killer T cells were collected from the control group (given physiological saline only), the group given Substance A and the group given Substance B, and the activity of the cellular immunocompetent cells was determined in terms of uptake of $^3$H-thymidine. The results are shown in Table 2.

TABLE 2

| | Cellular Immunocompetent Cell Activity ($^3$H-Thymidine Uptake Ratio) | |
| --- | --- | --- |
| | Macrophages | Killer T Cells |
| Control group (given physiological saline) | 100.0 | 100.0 |
| Group given substance A | 203.5 | 284.5 |
| Group given substance B | 157.2 | 233.7 |

It was found from the above results that Substance A exhibits stronger antitumor activity and immunopotentiating activity than those of Substance B.

EFFECT OF THE INVENTION

The above results indicate that immunopotentiating activity and tumor growth inhibitory activity are enhanced by removing the floating matter on the liquid or in the liquid or the adhering matter to the vessel wall occurring by adding alcohol at a final concentration of 20 to 60%, preferably at a final concentration of 20 to 50% by volume to the hot water extract from Grifola.

Hence, the feature of the present invention lies not in simply extracting polymeric β-glucan, but in effectively providing a glucan/protein complex having high immunopotentiating activity from limited resources by a simple method.

The substance obtained according to the present invention is of low toxicity and high safety and can be orally administered as health foods and pharmaceutical preparations, especially antitumor agent, in the form of tablets, capsules, liquid, syrup etc.

What is claimed is:

1. A glucan/protein complex produced by the steps of:
   (a) thermally extracting mycelia or fruit bodies of Grifola with water at a temperature of from 50° C. to 135° C.;
   (b) adding alcohol to the resulting water-soluble extract at a final concentration of 20 to 60% by volume, allowing said extract to stand in a vessel at a temperature of 1° to 25° C., and removing floating matter on the liquid or in the liquid or matter adhered to the vessel wall; and
   (c) addition alcohol to said extract at a final concentration of 80 to 99% by volume, allowing said extract to stand at 1° to 25° C., and recovering said glucan/protein complex in the form of precipitates.

2. A glucan/protein complex produced by the steps of:
   (a) thermally extracting mycelia or fruit bodies of Grifola with water at a temperature of from 50° C. to 135° C.;
   (b) adding alcohol to the resulting water-soluble extract at a final concentration of 20 to 50% by volume, allowing said extract to stand in a vessel at a temperature of 1° to 5° C., and removing floating matter on the liquid or in the liquid or matter adhered to the vessel wall; and
   (c) adding alcohol to said extract at a final concentration of 80 to 90% by volume, allowing said extract to stand at 1° to 5° C., and recovering said glucan/protein complex in the form of precipitates.

3. A glucan/protein complex produced by the steps of:
   (a) thermally extracting mycelia or fruit bodies of Grifola with water at a temperature of from 50° C. to 135° C.;

(b) adding alcohol to the resulting water-soluble extract at a final concentration of 20 to 60% by volume, allowing said extract to stand in a vessel at a temperature of 1° to 25° C., and removing floating matter on the liquid or in the liquid or matter adhered to the vessel wall; and (c) concentrating said extract to form said glucan/protein complex in the form of precipitates, or concentrating said extract into dryness to form said glucan/protein complex.

4. A glucan/protein complex produced by the steps of:

(a) thermally extracting mycelia or fruit bodies of Grifola with water at a temperature of from 50° C. to 135° C.;

(b) adding alcohol to the resulting water-soluble extract at a final concentration of 20 to 50% by volume, allowing said extract to stand in a vessel at a temperature of 1° to 5° C., and removing floating matter on the liquid or in the liquid or matter adhered to the vessel wall; and (c) concentrating the solution to form said glucan/protein complex in the form of precipitates, or concentrating said extract into dryness to form said glucan/protein complex.

5. The glucan/protein complex according to any one of claims 1, 2, 3 or 4, wherein the ratio of glucan to protein is in the range of from 80:20 to 99:1.

6. An antitumor agent having tumor-growth inhibition and cellular immunocompetent activity, which consists essentially of the glucan/protein complex of any one of claims 1, 2, 3 or 4 as an active ingredient.

7. The glucan/protein complex according to any one of claims 1, 2, 3 or 4, wherein Grifola is *Grifola frondosa, Grifola albicans Imaz, Grifola umbellatus* or *Grifola gigantea*.

8. The glucan/protein complex according to claim 2, wherein the ratio of glucan to protein is in the range of from 80:20 to 99:1.

9. The glucan/protein complex according to claim 3, wherein the ratio of glucan to protein is in the range of from 80:20 to 99:1.

10. The glucan/protein complex according to claim 4, wherein the ratio of glucan to protein is in the range of from 80:20 to 99:1.

11. An antitumor agent having tumor-growth inhibition and cellular immunocompetent activity, which consists essentially of the glucan/protein complex of claim 2 as an active ingredient.

12. An antitumor agent having tumor-growth inhibition and cellular immunocompetent activity, which consists essentially of the glucan/protein complex of claim 3 as an active ingredient.

13. An antitumor agent having tumor-growth inhibition and cellular immunocompetent activity, which consists essentially of the glucan/protein complex of claim 4 as an active ingredient.

14. An antitumor agent having tumor-growth inhibition and cellular immunocompetent activity, which consists essentially of the glucan/protein complex of claim 5 as an active ingredient.

15. The glucan/protein complex according to claim 2, wherein Grifola is *Grifola frondosa, Grifola albicans Imaz, Grifola umbellatus* or *Grifola gigantea*.

16. The glucan/protein complex according to claim 3, wherein Grifola is *Grifola frondosa, Grifola albicans Imaz, Grifola umbellatus* or *Grifola gigantea*.

17. The glucan/protein complex according to claim 4, wherein Grifola is *Grifola frondosa, Grifola albicans Imaz, Grifola umbellatus* or Grifola gigantea.

* * * * *